United States Patent
Taranta et al.

(10) Patent No.: US 10,383,327 B2
(45) Date of Patent: Aug. 20, 2019

(54) EMULSIFIABLE GRANULE OBTAINABLE BY MIXING AN PESTICIDAL EMULSION WITH SOLID DISPERSANT AND EXTRUDING THE RESULTING PASTE

(71) Applicant: BASF SE, Ludwigshafen (DE)

(72) Inventors: Claude Taranta, Stutensee (DE); Thomas Bork, Westhofen (DE); Jochen Schreieck, Schifferstadt (DE); Helmut Mueller, Weisenheim (DE); Nadine Riediger, Schifferstadt (DE); Clark D. Klein, Pittsboro, NC (US); Rebecca Willis, Garner, NC (US); Tatjana Sikuljak, Mannheim (DE); Simon Nord, Karlsruhe (DE)

(73) Assignee: BASF SE, Ludwigshafen am Rhein (DE)

( * ) Notice: Subject to any disclaimer, the term of this patent is extended or adjusted under 35 U.S.C. 154(b) by 634 days.

(21) Appl. No.: 14/381,102

(22) PCT Filed: Feb. 26, 2013

(86) PCT No.: PCT/EP2013/053816
§ 371 (c)(1),
(2) Date: Aug. 26, 2014

(87) PCT Pub. No.: WO2013/127790
PCT Pub. Date: Sep. 6, 2013

(65) Prior Publication Data
US 2015/0056257 A1    Feb. 26, 2015

Related U.S. Application Data

(60) Provisional application No. 61/605,782, filed on Mar. 2, 2012.

(30) Foreign Application Priority Data

Mar. 15, 2012  (EP) ..................... 12159692

(51) Int. Cl.
| A01N 25/02 | (2006.01) |
| A01N 25/04 | (2006.01) |
| A01N 25/14 | (2006.01) |
| A01N 25/12 | (2006.01) |
| A01N 43/653 | (2006.01) |
| A01N 43/90 | (2006.01) |
| A01N 47/24 | (2006.01) |
| A01N 53/00 | (2006.01) |
| A01N 47/40 | (2006.01) |

(52) U.S. Cl.
CPC .............. *A01N 25/04* (2013.01); *A01N 25/02* (2013.01); *A01N 25/12* (2013.01); *A01N 25/14* (2013.01); *A01N 43/653* (2013.01); *A01N 43/90* (2013.01); *A01N 47/24* (2013.01); *A01N 47/40* (2013.01); *A01N 53/00* (2013.01)

(58) Field of Classification Search
None
See application file for complete search history.

(56) References Cited

U.S. PATENT DOCUMENTS

| 5,703,010 A | 12/1997 | Heinrich et al. |
| 6,013,676 A | 1/2000 | Suzuki et al. |
| 6,841,613 B1 | 1/2005 | Taisne et al. |
| 2002/0117651 A1* | 8/2002 | Semen ................ B01J 2/28 252/399 |
| 2004/0110659 A1 | 6/2004 | Herault et al. |
| 2005/0019309 A1 | 1/2005 | Park et al. |
| 2008/0194709 A1 | 8/2008 | Hacaen |
| 2008/0200561 A1 | 8/2008 | Wirth et al. |
| 2010/0281584 A1 | 11/2010 | Horikoshi et al. |
| 2012/0302443 A1* | 11/2012 | Pentland ............. A01N 57/20 504/127 |

FOREIGN PATENT DOCUMENTS

| CN | 102187858 | 9/2011 |
| GB | 2 230 700 | 10/1990 |
| WO | WO 97/39626 | 10/1997 |
| WO | WO 2009/007999 | 1/2009 |
| WO | WO 2009103760 A2 * | 8/2009 ........... A01N 25/26 |
| WO | WO 2013/087417 | 6/2013 |

OTHER PUBLICATIONS

International Search Report dated Oct. 28, 2013, prepared in International Application No. PCT/EP2013/053816.
International Preliminary Report on Patentability dated Jun. 27, 2014, prepared in International Application No. PCT/EP2013/053816.
European Search Report from EP application No. 12159692, dated Aug. 20, 2012.

* cited by examiner

*Primary Examiner* — Nannette Holloman
(74) *Attorney, Agent, or Firm* — Brinks Gilson & Lione

(57) ABSTRACT

The present invention relates to a method for preparing an emulsifiable granule comprising the steps of a) emulsifying water with a solution of a pesticide in a water-insoluble solvent, b) contacting the emulsion resulting from step a) and a solid dispersant containing a water-soluble polycarboxylate and a water-soluble anionic surfactant, and c) extruding the paste resulting from step b). The invention further relates to emulsifiable granules containing a water-insoluble solvent, a pesticide, which is dissolved in the water-insoluble solvent, a water-soluble polycarboxylate, and a water-soluble anionic surfactant.

16 Claims, No Drawings

EMULSIFIABLE GRANULE OBTAINABLE BY MIXING AN PESTICIDAL EMULSION WITH SOLID DISPERSANT AND EXTRUDING THE RESULTING PASTE

This application is a National Stage application of International Application No. PCT/EP2013/053816, filed Feb. 26, 2013, which claims the benefit of U.S. Provisional Application No. 61/605,782, filed Mar. 2, 2012, the entire contents of which are hereby incorporated herein by reference. This application also claims priority under 35 U.S.C. § 119 to European Patent Application No. 12159692.8, filed Mar. 15, 2012, the entire contents of which is hereby incorporated herein by reference.

The present invention relates to a method for preparing an emulsifiable granule comprising the steps of a) emulsifying water with a solution of a pesticide in a water-insoluble solvent, b) contacting the emulsion resulting from step a) and a solid dispersant containing a water-soluble polycarboxylate and a water-soluble anionic surfactant, and c) extruding the paste resulting from step b). The invention further relates to emulsifiable granules containing a water-insoluble solvent, a pesticide, which is dissolved in the water-insoluble solvent, a water-soluble polycarboxylate, and a water-soluble anionic surfactant. The preferred embodiments of the invention mentioned herein below have to be understood as being preferred either independently from each other or in combination with one another.

Crop protection agents are formulated in solid or liquid compositions, usually in the form of a concentrate for ease of handling and transportation, which is diluted with water by the user before application. Liquid formulations in the form of emulsifiable concentrates contain a very high proportion of organic solvent (often up to 80 percent) which are increasingly coming under scrutiny for their effect on the environment; emulsion concentrates have a higher water content but still contain organic solvents. Suspension concentrates, another water-based liquid form, are often viscous giving rise to handling problems and loss of active ingredient through retention in the packaging. Solid formulations can also have disadvantages; the more common granules and powders in particular can be difficult to measure but more importantly can be dusty and pose inhalation hazards for the formulator and the user. Tablets have not been used extensively because they are often slow to dissolve. In addition, solid formulations have been found generally to possess a lower biological activity than liquid formulations. Also, with unsophisticated mixing techniques at the site of use, usually in a farmer's field, the tendency of solid forms not to emulsify immediately can cause not only clogging of spray equipment with undispersed formulation, but also an inadequate application of active ingredient to the crop to be treated. Thus there is a need for a fast-emulsifying solid crop protection formulation which has better handling characteristics and enhanced biological activity over conventional forms, to satisfy both environmental concerns and provide an effective, product for the farmer to use in an unsophisticated manner in the field. Object of the present invention was to overcome the above mentioned problems.

Emulsifiable granules and methods for their preparation are known: WO 2006/029718 discloses the preparation of emulsifiable granules by granulation of a pesticide-containing emulsion in a fluidized bed dryer. WO 1997/39626 discloses the preparation of emulsifiable granules by spray drying of a pesticide containing emulsion. GB 2230700 discloses the preparation of emulsifiable granules by spray drying of a pesticide containing emulsion.

The object was solved by a method for preparing emulsifiable granules comprising the steps of
a) emulsifying water with a solution of a pesticide in a water-insoluble solvent,
b) contacting the emulsion resulting from step a) and a solid dispersant containing a water-soluble polycarboxylate and a water-soluble anionic surfactant, and
c) extruding the paste resulting from step b).

The object was also solved by emulsifiable granules containing a water-insoluble solvent, a pesticide, which is dissolved in the water-insoluble solvent, a water-soluble polycarboxylate, and a water-soluble anionic surfactant.

Emulsifiable granules may form an emulsion (e.g. an oil-in-water emulsion) upon dilution with an excess (e.g. 10 fold amount) water at 20° C.

Based on the extrusion process, the granules may have the shape of an extrudate. In the case of circular holes of the extruder, the spaghetti-shaped extrudate may be cut into cylindrical shape. In case of polygonal holes (e.g. triangular or rectangular), the extrudate may be cut into corresponding shapes. The resulting pellets might be broken into shorter granules. Preferably, the resulting granules have cylindrical shape with a length of 0.2 to 10 mm and a diameter of 0.2 to 10 mm. In another preferred embodiment, the resulting granules have a shape, which has length of 0.2 to 10 mm at its most distant points, and a diameter of 0.2 to 10 mm at its broadest diameter.

The water-insoluble solvent may have a solubility in water of up to 20 g/l, preferably up to 4 g/l, and in particular up to 1.5 g/l, each at 25° C.

The water-insoluble solvent may have a boiling point of at least 110° C., preferably at least 140° C., and in particular at least 170° C.

The water-insoluble solvent may have a flash point of at least 60° C., preferably at least 80° C., and in particular at least 100° C.

Suitable examples of water-insoluble solvents are
N—$C_4$-$C_{12}$-alkylpyrrolidone, preferably N—$C_6$-C10-alkylpyrrolidone, e.g. N-octylpyrrolidone;
N,N-dimethyl $C_6$-$C_{14}$ alkanamides, preferably N,N-dimethyl $C_8$-$C_{12}$ alkanamides;
$C_5$-$C_{12}$-alkyl lactates, preferably C6-$C_{10}$-alkyl lactates, e.g. 2-ethylhexyl lactate;
aliphatic and/or aromatic hydrocarbons having a boiling point of at least 140° C., preferably aromatic hydrocarbons having a boiling point of at least 180° C.;
$C_1$-$C_{12}$ alkylphenols, preferably $C_2$-$C_{10}$ alkylphenols, e.g. 2-(1-methylpropyl)phenol;
$C_4$-$C_{22}$ alkyl or $C_6$-$C_{22}$ aryl benzoate, preferably $C_6$-$C_{12}$ aryl benzoate, e.g. benzyl benzoate; and
di-$C_4$-$C_{22}$ alkyl phthalates, preferably di-$C_6$-$C_{14}$ alkyl pthalates, e.g. diisononyl phthalate.

Mixtures of water-insoluble solvents are also suitable.

The water-insoluble solvent may contain minor amounts of water-soluble solvents, e.g. up to 30 wt %, preferably up to 10 wt %, and in particular up to 3 wt %. Water-soluble solvents are organic solvents, which may have a solubility in water of at least 10 g/l, preferably at least 50 g/l, and in particular at least 100 g/l.

The water-insoluble or water-soluble solvents may be selected from the following list of examples according to their solubility in water:mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g.

cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

The solid dispersant contains a water-soluble polycarboxylate, and a water-soluble anionic surfactant, and optionally further solid auxiliaries. The solid dispersant may be present as a powder or dust. It is usually solid at 25° C., or it may have a melting point of at least 30° C., preferably at least 50° C.

The water-soluble polycarboxylate is soluble in water, e.g. at least 50 g/l, preferably at least 100 g/l, each at 20° C. The water-soluble polycarboxylate may have a melting point of above 30° C., preferably above 60° C., and in particular above 100° C. Polycarboxylates are polymers, which may comprise carboxylic acid groups in free acid form and/or as salt. More specifically, polycarboxylates are copolymers of ethylenically unsaturated carboxylic acid and/or anhydride.

Preferred water-soluble polycarboxylates are copolymers of at least one ethylenically unsaturated carboxylic acid and/or anhydride, and of at least one ethylenically unsaturated nonionic monomer. More preferred polycarboxylates are copolymers of an ethylenically unsaturated, linear or branched aliphatic, cycloaliphatic or aromatic monocarboxylic or polycarboxylic acid or anhydride and of alpha-monoolefins containing from 2 to 20 carbon atoms.

Suitable acid or anhydride monomers are those containing from 3 to 10 carbon atoms, preferably those of formula $(R^1)(R^2)C=C(R^3)COOH$, in which $R^1$, $R^2$ and $R^3$ are identical or different and represent independently form another
a hydrogen atom,
a hydrocarbon-based radical containing from 1 to 4 carbon atoms (preferably methyl),
a —COOH function,
a radical —R—COOH, in which R represents a hydrocarbon-based residue containing from 1 to 4 carbon atoms, preferably an alkylene residue containing 1 or 2 carbon atoms, most particularly methylene. Mixtures of such monomers are also suitable.

Preferentially, at least one of the radicals $R^1$ and $R^2$ is hydrogen. In particular, the acid or anhydride monomers are selected from acrylic, methacrylic, crotonic, maleic, fumaric, citraconic or itaconic acid or anhydride, wherein maleic acid and/or its anhydride are most preferred.

Suitable ethylenically unsaturated nonionic monomers are alpha-monoolefin monomers, such as ethylene, propylene, 1-butene, isobutylene, n-1-pentene, 2-methyl-1-butene, n-1-hexene, 2-methyl-1-pentene, 4-methyl-1-pentene, 2-ethyl-1-butene, diisobutylene (or 2,4,4-trimethyl-1-pentene) and 2-methyl-3,3-dimethyl-1-pentene. Mixtures of such monomers are also suitable.

The molar ratio between ethylenically unsaturated nonionic monomers and acid or anhydride monomers may be in the range from 20/80 to 80/20, preferably from 30/70 to 70/30, and in particular from 40/60 to 60/40. The molecular weight of the polycarboxylate may be 1 to 40 kDa, preferably 2 to 20 kDa, and in particular 3 to 14 kDa.

The water-soluble anionic surfactant is soluble in water, e.g. at least 50 g/l, preferably at least 100 g/l, each at 20° C. The water-soluble anionic surfactant may have a melting point of above 100° C., preferably above 150° C., and in particular above 200° C. Suitable water-soluble anionic surfactants are alkali, alkaline earth or ammonium salts of sulfonates, sulfates, phosphates, carboxylates, and mixtures thereof. Examples of sulfonates are sulfonated phenol-formaldehyde condensation products, sulfonated cresol-formaldehyde condensation products, alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Preferred water-soluble anionic surfactants are alkali, alkaline earth or ammonium salts of sulfonates or sulfates, such as alkali salts of sulfonated and/or sulfated phenol-formaldehyde condensation products, sulfonated and/or sulfated cresol-formaldehyde condensation products (e.g. CAS 115535-44-9). Typically the sulfates or sulfonates have a molecular weight from 200 to 2000 g/mol, preferably from 250 to 1000 g/mol.

The term pesticide refers to at least one active substance selected from the group of the fungicides, insecticides, nematicides, herbicides, safeners and/or growth regulators. Preferred pesticides are fungicides, insecticides, and herbicides. Mixtures of pesticides of two or more of the above-mentioned classes may also be used. The skilled worker is familiar with such pesticides, which can be found, for example, in the Pesticide Manual, 15th Ed. (2009), The British Crop Protection Council, London. Examples of pesticides may be selected from the following list (groups A) to L) are fungicides):

A) Respiration inhibitors
Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methylacetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-

1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl) pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S,3R)-3-(2-chlorophenyl)-2-(2,4-difluorophenyl)-oxiranylmethyl]-5-thiocyanato-1H[1,2,4]triazole, 2-[rel(2S,3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic acid synthesis inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(ptolylmethoxy)pyrimidin-4-amine, 5-fluoro-2-(4-fluorophenylmethoxyl)pyrimidin-4-amine;

D) Inhibitors of cell division and cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of amino acid and protein synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal transduction inhibitors
MAP/histidine kinase inhibitors: fluoroimid, iprodione, procymidone, vinclozolin, fenpiclonil, fludioxonil;
G protein inhibitors: quinoxyfen;

G) Lipid and membrane synthesis inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acids: propamocarb, propamocarb-hydrochlorid
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell wall synthesis inhibitors
inhibitors of glucan synthesis: validamycin, polyoxin B;
melanin synthesis inhibitors: pyroquilon, tricyclazole, carpropamid, dicyclomet, fenoxanil;

J) Plant defence inducers
acibenzolar-S-methyl, probenazole, isotianil, tiadinil, prohexadione-calcium; phosphonates: fosetyl, fosetyl-aluminum, phosphorous acid and its salts;

K) Unknown mode of action
bronopol, chinomethionat, cyflufenamid, cymoxanil, dazomet, debacarb, diclomezine, difenoquat, difenoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)phenyl)-N-ethyl-N-methyl formamidine, 2-{1-[2-(5-methyl-3-trifluoromethyl-pyrazole-1-yl) acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)- acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators:
*Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives: bilanafos, glyphosate, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;
phenoxy acetic acids: clomeprop, 2,4-dichlorophenoxyacetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methylphenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

In another preferred embodiment, the pesticide is selected from a pyripyropene pesticide of formula I or of formula II Formula I

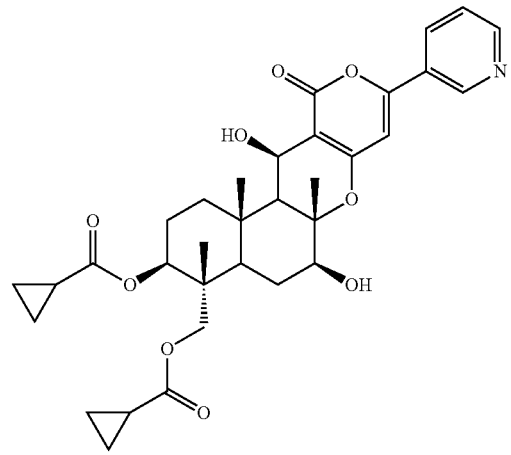

Formula II

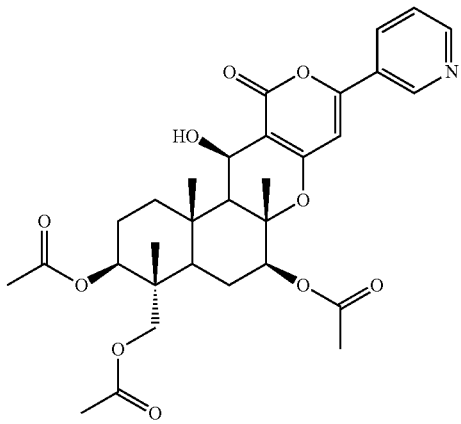

The pyripyropene pesticide of formula (I) is known from WO 2009/081851 (Examples, compound 4) and belongs to the class of pyripyropene derivatives. Pyripyropene A (pyripyropene pesticide of formula II) may be produced e.g. by the method described in Journal of Society of Synthetic Organic Chemistry, Japan (1998), Vol. 56, No. 6, pp. 478-488 or WO 94/09417.

In another preferred embodiment, the pesticide is selected from any pesticide with the exception of the pyripyropene pesticide of formula I and of formula II.

The pesticide is preferably is insoluble in water. For example, the pesticide has a solubility in water of up to 10 g/l, preferably up to 2 g/l, and in particular up to 0.5 g/l, at 20° C.

The pesticide is preferably soluble in the water-insoluble solvent (e.g. N-octylpyrrolidone), for example at least 10 g/l, preferably at least 50 g/l, and in particular at least 100 g/l, each at 25° C.

The emulsifiable granules contains at least one pesticide, which is dissolved in the water-insoluble solvent, usually at 20° C. Minor amounts of said pesticide may be present in solid form, e.g. up to 40 wt %, preferably up to 10 wt %, and in particular up to 3 wt %, based on the total amount of the pesticide.

The emulsifiable granules may contain further pesticides, which are not dissolved in the water-insoluble solvent, but rather for example present in solid state in the granules. Suitable further pesticides are pesticides, which are soluble in water, e.g. at least 10 g/l, preferably at least 50 g/l at 20° C.

The emulsifiable granules may comprise formulation auxiliaries. Suitable formulation auxiliaries are solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers, effervescent, and binders.

Suitable solid carriers or fillers fertilizers, e.g. ammonium sulfate, ammonium phosphate, ammonium nitrate, ureas; sugars, e.g. mono- or di-saccharides, mono- or di-saccharides, oligosaccharides, homopolymers of vinylpyrrolidone, copolymers of vinylpyrrolidone, which comprise at least 80 mol % of vinylpyrrolidone (based on the total amount of monomers in the copolymer), or mixtures thereof. Solid carriers may be solid at 25° C. Preferred solid carriers are water-soluble, which may have a solubility in water at 20° C. of at least 3 wt %, preferably at least 7 wt %, and in particular at least 10 wt %.

In a preferred form the emulsifiable granule contains a polyvinylpyrrolidone, such as homopolymers of vinylpyrrolidone, copolymers of vinylpyrrolidone, which comprise at least 80 mol % of vinylpyrrolidone (based on the total amount of monomers in the copolymer), or mixtures thereof. Suitable polyvinylpyrrolidones (e.g. homopolymers of vinylpyrrolidones) have a solubility in water at 20° C. of at least 3 wt %, preferably at least 7 wt %, and in particular at least 10 wt %.

In another preferred solid carriers are mono- or di-saccharides, especially monosaccharides, such as lactose.

In another preferred form solid carriers are mono- or di-saccharides, or homopolymers of vinylpyrrolidone, or mixtures thereof. More preferred solid carriers are monosaccharides (e.g. lactose), homopolymers of vinylpyrrolidone, or mixtures thereof.

Suitable effervescent is a combination of a hydrogen carbonate and an organic acid, such as a combination of citric acid and potassium hydrogencarbonate. Examples of the hydrogen carbonate include sodium hydrogen carbonate, potassium hydrogen carbonate and ammonium hydrogen carbonate. Examples of the organic acid include citric acid, succinic acid, malic acid, lactic acid, tartaric acid, fumaric acid and maleic acid. The organic acid is preferably used in an amount of 0.5 percent by weight to 20 percent by weight and, particularly, 1 percent by weight to 10 percent by weight based on the whole weight. The organic acid may be used alone or as a mixture of two or more of them. The hydrogencarbonate can be preferably used in an amount of 0.25 times to 2 times by molar ratio of the amount of the organic acid.

Suitable surfactants are surface-active compounds, such as anionic, cationic, nonionic and amphoteric surfactants, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

In addition to the water-soluble anionic surfactant further anionic surfactants may be added. Typically, the further anionic surfactant is selected from anionic surfactants, which are different from the water-soluble anionic surfactant. Suitable further anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are vinylalcohols or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylate thickeners, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

The emulsifiable granule may contain at least 2%, preferably at least 4 wt %, and in particular at least 7 wt % of the water-insoluble solvent. The emulsifiable granule may contain 3 to 60 wt %, preferably 5 to 50 wt %, and in particular 8 to 40 wt % of the water-insoluble solvent, such as are N—$C_4$-$C_{12}$-alkylpyrrolidone, N,N-dimethyl $C_8$-$C_{12}$ alkanamides, $C_5$-$C_{12}$-alkyl lactates, aliphatic and/or aromatic hydrocarbons having a boiling point of at least 140° C., or mixtures thereof.

The emulsifiable granule may contain at least 1%, preferably at least 2.5 wt %, and in particular at least 4 wt % of the pesticide. The emulsifiable granule may contain 0.1 to 35 wt %, preferably 1 to 25 wt %, and in particular 2.5 to 17 wt % of the pesticide, such as water-insoluble pesticides.

The emulsifiable granule may contain at least 5%, preferably at least 12 wt %, and in particular at least 20 wt % of the water-soluble polycarboxylate. The emulsifiable granule may contain 10 to 80 wt %, preferably 15 to 70 wt %, and in particular 22 to 60 wt % of the water-soluble polycarboxylate, such as copolymers of an ethylenically unsaturated, linear or branched aliphatic, cycloaliphatic or aromatic monocarboxylic or polycarboxylic acid or anhydride and of alpha-monoolefins containing from 2 to 20 carbon atoms.

The emulsifiable granule may contain at least 0.5%, preferably at least 2 wt %, and in particular at least 3 wt % of the water-soluble anionic surfactant. The emulsifiable granule may contain 0.2 to 50 wt %, preferably 1 to 30 wt %, and in particular 2 to 15 wt % of the water-soluble anionic surfactant, such as sulfonates.

The emulsifiable granule may contain at least 0.5%, preferably at least 2 wt %, and in particular at least 3 wt % of the water-soluble solid carrier. The emulsifiable granule may contain up to 65%, preferably up to 55 wt %, and in particular up to 45 wt % of the water-soluble solid carrier.

The emulsifiable granule may contain 0 to 65 wt %, preferably 1 to 55 wt %, and in particular 3 to 45 wt % of the water-soluble solid carrier, such as mono- or di-saccharides, homopolymers of vinylpyrrolidone, or mixtures thereof.

Preferably, the emulsifiable granule may contain
5 to 50 wt % of the water-insoluble solvent,
1 to 25 wt % of the pesticide,
15 to 70 wt % of the water-soluble polycarboxylate,
1 to 30 wt % of the water-soluble anionic surfactant,
and optionally formulation auxiliaries (e.g. water-soluble solid carrier) filled up to 100 wt %.

More preferably, the emulsifiable granule may contain
8 to 40 wt % of the water-insoluble solvent,
3 to 20 wt % of the pesticide,
20 to 60 wt % of the water-soluble polycarboxylate,
2 to 15 wt % of the water-soluble anionic surfactant,
and optionally formulation auxiliaries (e.g. water-soluble solid carrier) filled up to 100 wt %.

The weight ratio of the water-soluble polycarboxylate to the water-soluble anionic surfactant may be in the range from 30:1 to 1:3, preferably from 20:1 to 1:1, and in particular from 15:1 to 2:1.

The weight ratio of the water-soluble polycarboxylate to the water-insoluble solvent may be in the range from 15:1 to 1:2, preferably from 8:1 to 1:2, and in particular from 4:1 to 1:1.5.

The weight ratio of the sum of the water-soluble polycarboxylate and the water-soluble anionic surfactant to the water-insoluble solvent may be in the range from 20:1 to 1:3, preferably from 8:1 to 1:2, and in particular from 5:1 to 1.2:1.

The weight ratio of the sum of the water-soluble polycarboxylate, the water-soluble anionic surfactant and the water-soluble solid carrier to the water-insoluble solvent may be in the range from 20:1 to 1:3, preferably from 10:1 to 1:1.5, and in particular from 7:1 to 1.1:1.

The method for preparing the emulsifiable granule may comprise the steps of
a) emulsifying of water with a solution of a pesticide in a water-insoluble solvent,
b) contacting the emulsion resulting from step a) and a solid dispersant containing a water-soluble polycarboxylate, and a water-soluble anionic surfactant,
c) extruding the paste resulting from step b), and
d) optionally drying the extrudate resulting from step c).

The emulsifiable granules are preferably obtainable (in particular they are obtained) by the method according to the invention. The steps a) to d) are usually performed in the given order.

The steps of emulsifying water with a solution of a pesticide in a water-insoluble solvent may be achieved by any conventional emulsifying method. Typically, the pesticide is first dissolved in the water-insoluble solvent, followed by addition of water, and subsequent emulsification, e.g. by stirring, or applying high shear. Step a) usually results in a oil-in-water emulsion. Step a) may be performed at temperatures from 3 to 95° C., preferably at 10 to 40° C. Further formulation auxiliaries may already be added to the water or water-insoluble solvent. For example, water-soluble formulation auxiliaries may be added to the water. The droplet size of the emulsified droplets may be from 0.1 to 10 μm, preferably from 0.5 to 3 μm.

When employed in plant protection, the amounts of pesticides (also called active substances) applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

The user applies the solid composition after preparing an aqueous tank mix usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The contacting of the emulsion resulting from step a) and the solid dispersant containing a water-soluble polycarboxylate, and a water-soluble anionic surfactant usually yields a paste, which may be an extrudable paste. Extrudable pastes have such a liquid content (e.g. water content) that results in a extrudate which keeps its shape for at least 1 h at 20° C. Preferably, the paste resulting from step b) contains less than 30 wt % water, more preferably less than 20 wt %, in particular less than 17 wt %, based on the total weight of the paste. Preferably, the paste resulting from step b) contains less than 50 wt % (more preferably less than 40 wt %, in particular less than 35 wt %) water-insoluble solvent, based on the total weight of the paste. The paste resulting from step b) may contain at least 30 wt %, more preferably at least 35 wt %, and in particular at least 40 wt %, of the sum of the water-soluble polycarboxylate and the water-soluble anionic surfactant, based on the total weight of the paste. The paste resulting from step b) may contain at least 35 wt %, more preferably at least 42 wt %, and in particular at least 46 wt %, of the sum of the water-soluble polycarboxylate, the water-soluble anionic surfactant, and the water-soluble solid carrier, based on the total weight of the paste.

The step c) of extruding the paste resulting from step b) usually results in an extrudate. The extrusion may be performed on conventional extruding devices. The extrusion in step c) may be performed at a temperature below 60° C., preferably below 45° C., and in particular below 35° C. Said temperature refers to the paste during extrusion. When necessary, the temperature is maintained at the desired value by cooling.

The expert will adjust the water content of the extrudable paste in order to achieve an extrudable texture of the paste. Extruders are well known in the art. For example, a one screw or twin screw extruder may be used. Also extruders used for producing spaghetti may be used. Typically, the extrusion is accomplished at a pressure (usually taken just before entering into the extrusion grid) from 1 to 80 bars, preferably from 1 to 60 bars, and more preferably from 1 to 40 bars.

An extrusion grid may be used with holes of any shape, preferably of circular shape. Typically, the diameter of the holes is from 0.2 to 5.0 mm, preferably from 0.5 to 3 mm, more preferably from 0.5 to 2.0 mm.

The stick-like extrudate may be cut, e.g. with a rotating knife, into shorter sticks before or after drying, preferably before drying. In the case of circular holes, the spaghetti-shaped extrudate may be cut into cylindrical shape. In case of polygonal holes (e.g. triangular or rectangular), the extrudate may be cut into corresponding shapes. The resulting pellets might be broken into shorter granules before or after drying, preferably after drying.

Optionally, in step d) the drying the extrudate resulting from step c) may be performed by conventional drying means, such as by heated air or vacuum. Drying may be done by the application of elevated temperatures, such as hot air, from 30 to 150° C., preferably from 50 to 80° C.

The heating time depends on the temperature, the size of the extrudate and the desired amount of water in the final product. The drying may result in emulsifiable granules which contain up to 10 wt %, preferably up to 5 wt %, and in particular up to 2 wt % water.

The present invention further relates to a sprayable emulsion (e.g. a tank mix) obtainable by contacting water and the emulsifiable granules according to the invention or the granules obtained by the method according to the invention. The sprayable emulsion may contain from 0.02 to 2 wt %, preferably from 0.05 to 0.5 wt % of the emulsifiable granules. The term sprayable means that the emulsion may be sprayed with conventional spraying agrochemical means. The droplet size of the emulsified droplets may be from 0.1 to 10 μm, preferably from 0.5 to 3 μm.

The present invention further relates to a method for controlling phytopathogenic fungi and/or undesired plant growth and/or undesired attack by insects or mites and/or for regulating the growth of plants, where the emulsifiable granules according to the invention or the emulsifiable granules obtained by the method according to the invention are allowed to act on the particular pests, their habitat or the plants to be protected from the particular pest, the soil and/or on undesired plants and/or the useful plants and/or their habitat.

When employed in plant protection, the amounts of pesticides (also called active substances) applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

The user applies the emulsifiable granules after preparing an aqueous tank mix (e.g. the sprayable emulsion) usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The present invention offers various advantages: The emulsifiable granules emulsify rapidly upon mixing with water; they do hardly tend to baking; they are easily flowable; they have only a low organic solvent content; they have a high bioefficacy, optionally even without additional adjuvants; contain only a reduced amount of expensive polymers (e.g. expensive polyvinylpyrrolidone, or polyvinyl alcohol). The method according to the invention may use a low temperature extrusion; the method is very mild, so even temperature sensitive pesticides may be formulated. The method is very sustainable, especially in comparison to spray drying or fluid bed technologies: it requires less energy, less water, produces less waste, or the machines are easy to clean.

EXAMPLES

S1: N-octylpyrrolidon
S2: Mixture of 50-65 wt % N,N-dimethyloctanamide and 37-50 wt % N,N-dimethyldecanamide.
S3: (S)-2-ethylhexyllactate
S4: Technical mixture of aromatic hydrocarbons, boiling point above 210° C., freezing point below −8° C.
A1: Aqueous solution (25 wt %) of water soluble sodium salt of a copolymer prepared from maleic anhydride and diisobutylene (molar ratio about 1/1), molecular weight about 4-8 kDa.
A2: Lactose
A3: Poly(vinylpyrrolidone), water-soluble powder, K-value in water 26-34, melting point above 130° C.
A4: $C_{16}$-$C_{18}$ alcohol ethoxylate propoxylate.
A5: Silicon based defoamer.
A6: Ethoxylated short fatty alcohol, molecular weight about 430 g/mol, soluble in water (>10 wt %).
A7: anionic dispersant, dodecylbenzenesulphonic acid, calcium salt (70 wt %) in isobutanol.
D1: water soluble anionic dispersant, powdery sodium salt of sulfurous acid reaction products with cresol-formaldehyde-nonylphenol polymer, pH 7-8 in water at 5 wt % concentration, molecular weight 300-900 g/mol.
D2: water soluble anionic dispersant, powdery copolymer of maleic anhydride and diisobutylene (sodium salt; molar ratio of monomers 7/3 to 3/7).

Example 1—Preparation of Emulsifiable Granules of Pyraclostrobin

1) Preparation of an Emulsion

The pyraclostrobin ("Active") was dissolved in the solvent or solvent mixture (S1, S2, S3). Water, part of the amount of the dispersant D2 and optionally water-soluble additive A1 was added and the mixture emulsified at 1800 rpm for about 4 min at room temperature.

2) Preparation of a Extrudable Paste

The solid dispersants D1 and D2, and optionally further solid auxiliaries (e.g. A2, A3, A4) or the liquid additives (e.g. A5, or A6) were mixed. The emulsion of step 1) was sprayed on said mixture and knedded to result in a paste.

3) Extrusion

The paste of step 2) was extruded at room temperature. The extrudate was dried in an air stream at 50° C. The final granules had an average cross section of about 1 mm and a length of about 2-4 mm.

Five different samples A to E were prepared. The amounts of the ingredients are summarized in Table 1, wherein all components except water add up to 100%. Water was removed by the drying step to achieve a final water content in the granules of about 1 wt %.

TABLE 1

| | Ingredients (wt %) | | | | | | | | | | | |
|---|---|---|---|---|---|---|---|---|---|---|---|---|
| | Active | S1 | S2 | S4 | $H_2O$ | A1 | D1 | D2 | A2 | A3 | A4 | A5 | A7 |
| A | 10 | 15 | — | 14 | 3 | 3 | 10 | 35 | 3.2 | 8.5 | — | 0.3 | 1 |
| B | 10 | 15 | — | 14 | 3 | 3 | 5 | 40 | — | 7.7 | 5 | 0.3 | — |
| C | 10 | 15 | — | 14 | 3 | 6 | 5 | 40 | — | 4.7 | 5 | 0.3 | — |
| D | 10 | 15 | — | — | 14 | — | 10 | 40.5 | 20 | 4 | — | 0.5 | — |
| E | 10 | — | 15 | — | 14 | — | 10 | 40.5 | 20 | 4 | — | 0.5 | — |

Example 2—Preparation of Emulsifiable Granules of Metconazol

The emulsifiable granules of metconazol were prepared by the method describe in Example 1 and the ingredients are summarized in Table 2.

TABLE 2

| | Ingredients (wt %) | | | | | | | | | |
|---|---|---|---|---|---|---|---|---|---|---|
| | Active | S1 | S4 | $H_2O$ | A1 | D1 | D2 | A3 | A5 | A6 | A7 |
| A | 10 | 15 | 14 | 3 | 3 | 10 | 39 | 7.7 | 0.3 | — | 1 |
| B | 6 | 8 | 7 | 3 | 3 | 5 | 52 | 8.7 | 0.3 | 10 | — |
| C | 6 | 8 | 7 | 3 | 12 | 5 | 47 | 4.7 | 0.3 | 10 | — |

Example 3—Preparation of Emulsifiable Granules of Alpha-Cypermethrin

The emulsifiable granules of metconazol were prepared by the method describe in Example 1 and the ingredients are summarized in Table 3.

TABLE 3

| | Ingredients (wt %) | | | | | | | | | |
|---|---|---|---|---|---|---|---|---|---|---|
| | Active | S1 | S4 | $H_2O$ | A1 | D1 | D2 | A2 | A3 | A5 | A7 |
| A | 10 | 15 | 14 | 3 | 3 | 10 | 35 | 6.7 | 5 | 0.3 | 1 |
| B | 10 | 15 | 14 | 3 | 3 | 10 | 35 | 6.7 | 5 | 0.3 | 1 |

Example 4—Preparation of Emulsifiable Granules of Pyripyropene

The emulsifiable granules of the pyripyropene of Formula I were prepared by the method describe in Example 1 and the ingredients are summarized in Table 4.

TABLE 4

| | Ingredients (wt %) | | | | | | | | | | |
|---|---|---|---|---|---|---|---|---|---|---|---|
| | Active | S1 | S2 | S3 | S4 | H$_2$O | A1 | D1 | D2 | A2 | A3 | A5 |
| A | 5 | 15 | — | — | 14 | 3 | 3 | 10 | 40 | 5.7 | 7 | 0.3 |
| B | 5 | — | 12 | — | — | 14 | — | 10 | 33 | 35.5 | 4 | 0.5 |
| C | 5 | 15 | — | — | — | 14 | — | 10 | 33 | 32.5 | 4 | 0.5 |
| D | 5 | — | — | 15 | — | 14 | — | 10 | 33 | 32.5 | 4 | 0.5 |

The invention claimed is:

1. A method for preparing emulsifiable granules, comprising the steps of
   a) emulsifying water with a solution of a pesticide in a water-insoluble solvent,
   b) contacting the emulsion resulting from step a) and a solid dispersant containing a water-soluble polycarboxylate and a water-soluble anionic surfactant, and
   c) extruding the paste resulting from step b);
      wherein the paste resulting from step b) contains less than 30 wt % water, based on the total weight of the paste; and
      wherein the emulsifiable granules contain at least 0.5 wt % of a water soluble solid carrier.

2. The method according to claim 1, wherein the extrusion in step c) is performed at a temperature below 60° C.

3. The method according to claim 1, wherein the paste resulting from step b) contains less than 40 wt % water-insoluble solvent, based on the total weight of the paste.

4. The method according to claim 1, wherein the paste resulting from step b) contains at least 35 wt % of the sum of the water-soluble polycarboxylate and the water-soluble anionic surfactant, based on the total weight of the paste.

5. The method according to claim 1, wherein the granules have the shape of an extrudate, which has a cylindrical or a polygonal shape.

6. Emulsifiable granules containing
   a water-insoluble solvent,
   a pesticide, which is dissolved in the water-insoluble solvent,
   a water-soluble polycarboxylate, which is a copolymer of at least one ethylenically unsaturated carboxylic acid and/or anhydride, and of at least one ethylenically unsaturated nonionic monomer,
   a water-soluble anionic surfactant, and
   a water-soluble solid carrier,
   wherein the granules are obtainable by the method as defined in claim 1.

7. The granules according to claim 6 in the shape of an extrudate, which has a cylindrical or a polygonal shape.

8. The granules according to claim 6, containing
   5 to 50 wt % of the water-insoluble solvent,
   1 to 25 wt % of the pesticide,
   15 to 70 wt % of the water-soluble polycarboxylate,
   1 to 30 wt % of the water-soluble anionic surfactant,
   and optionally formulation auxiliaries filled up to 100 wt %.

9. The granules according to claim 6, wherein the weight ratio of the water-soluble polycarboxylate to the water-soluble anionic surfactant is from 20:1 to 1:1.

10. The granules according to claim 6, wherein the weight ratio of the sum of the water-soluble polycarboxylate and the water-soluble anionic surfactant to the water-insoluble solvent is from 10:1 to 1:2.

11. The granules according to claim 6, wherein the water-soluble solid carrier is selected from mono- or di-saccharides, homopolymers of vinylpyrrolidone, copolymers of vinylpyrrolidone, which comprise at least 80 mol % of vinylpyrrolidone based on the total amount of monomers in the copolymer, or mixtures thereof.

12. The granules according to claim 10, wherein the solid carrier is selected from mono- or di-saccharides, homopolymers of vinylpyrrolidone, and mixtures thereof.

13. The granules according to claim 6, containing 1 to 55 wt % of the water-soluble solid carrier.

14. The granules according to claim 6, wherein the weight ratio of the sum of the water-soluble polycarboxylate, the water-soluble anionic surfactant and the water-soluble solid carrier to the water-insoluble solvent is in the range from 10:1 to 1:1.5.

15. A sprayable emulsion obtainable by contacting water and the emulsifiable granules as defined in claim 6 or the emulsifiable granules obtained by the method as defined in claim 1.

16. A method for controlling phytopathogenic fungi and/or undesired plant growth and/or undesired attack by insects or mites and/or for regulating the growth of plants, where the emulsifiable granules as defined in claim 1, or the emulsifiable granules obtained by the method as defined in claim 1 are allowed to act on the particular pests, their habitat or the plants to be protected from the particular pest, the soil and/or on undesired plants and/or the useful plants and/or their habitat.

* * * * *